United States Patent [19]
Nitzsche et al.

[11] Patent Number: 5,325,856
[45] Date of Patent: Jul. 5, 1994

[54] METHOD AND APPARATUS FOR ANALYZING CARDIAC ACTIVITY FOR IMPLANTABLE TACHYCARDIA DETECTION AND TREATMENT

[75] Inventors: Remi Nitzsche, Beynes; Marcel Limousin, Montrouge; Peter Jacobson, Haguenau, all of France

[73] Assignee: ELA Medical, Montrouge, France

[21] Appl. No.: 995,033

[22] Filed: Dec. 22, 1992

[30] Foreign Application Priority Data

Dec. 31, 1991 [FR] France ................. 91 16365

[51] Int. Cl.$^5$ ......................................... A61B 5/0464
[52] U.S. Cl. ..................................... 128/703; 607/14
[58] Field of Search ............... 128/703, 705; 607/14

[56] References Cited

U.S. PATENT DOCUMENTS

| | | | |
|---|---|---|---|
| 3,554,187 | 1/1971 | Glassner et al. | 128/703 |
| 3,608,882 | 9/1971 | Abe et al. | 128/703 |
| 3,946,725 | 3/1976 | Bolshov et al. | 128/2.06 R |
| 4,181,135 | 1/1980 | Andresen et al. | 128/703 |
| 4,860,749 | 8/1989 | Lehmann | 128/419 PG |

FOREIGN PATENT DOCUMENTS

| | | | |
|---|---|---|---|
| 0360412 | 3/1990 | European Pat. Off. | A61N 1/365 |
| 0395242 | 10/1990 | European Pat. Off. | A61N 1/39 |
| 0401962 | 12/1990 | European Pat. Off. | A61N 1/368 |
| 0436517 | 10/1991 | European Pat. Off. | A61N 1/368 |

OTHER PUBLICATIONS

R. A. Dufault et al., Comouters in Cardiology "Dual Lead Fibrillation Detection For Implantable Defibrillators Via LMS Algorithm", Oct. 7, 1986, Boston US, pp. 163–166.

K. B. Otte et al., "Physiologische Elektrostimulation des Herzens Stand und Entwicklungsaussichten" Medizintechnik, Sep. 1984, pp. 84–91.

Von Kurt-Bernd Otte et al., "Physiologische Elektrostimulation des Herzens Stand Und Entwicklungsaussichten", 4550 Medizintechnik, 24 (1984) Sep., No. 3, Berlin, DD., p. 91.

Primary Examiner—William E. Kamm
Attorney, Agent, or Firm—Davis Hoxie Faithfull & Hapgood

[57] ABSTRACT

The difference between the divergences between the determined PR and RR intervals (dPR−dRR) is measured, cycle by cycle, and compared to two selected thresholds S1 and S2. If the difference exceeds threshold S1, a signal corresponding to a ventricular tachycardia is triggered. If the difference is below threshold S2, a signal corresponding to a supraventricular tachycardia related signal is triggered. The trigger signals may be used to control the therapeutic treatment of an implantable tachycardia treatment device accordingly.

42 Claims, 1 Drawing Sheet

METHOD AND APPARATUS FOR ANALYZING CARDIAC ACTIVITY FOR IMPLANTABLE TACHYCARDIA DETECTION AND TREATMENT

FIELD OF THE INVENTION

This invention relates to cardiac arrhythmia treatment systems, more particularly to systems for reducing tachycardia. Such systems can be an integral part of a cardiac pacemaker for anti-arrhythmia purposes and/or an implantable defibrillator.

BACKGROUND OF THE INVENTION

Tachycardias are pathological accelerations of the heart rhythm. They can be classified into two distinctive categories based on the focus of their origin. Thus, a distinction is made between supraventricular tachycardia (SVT), which originates in the atrium, and ventricular tachycardia (VT), which originates in the ventricle. There is a suitable mode of treatment for each of these tachycardia based on delivery stimulation pulses of electric energy.

For SVTs, there are several possible known modes of treatment ranging from the absence of specific treatment to emitting stimulation pulses having an energy limited to a few micro-joules.

For VTs, it is known to be sometimes necessary to apply an electric shock stimulus of a few joules as soon as possible after the phenomenon has been observed. Such electric shocks are usually unpleasant and painful for patients and must be applied advisedly.

It is, therefore, important, when analyzing cardiac signals in the event of detection of an acceleration of the heart rhythm, to distinguish whether the situation is that of SVT or VT to avoid unnecessary shocks.

French patent No. 2,598,920 describes a system which senses the cardiac signal in the ventricle and detects therefrom the accelerations and decelerations of the heart rhythm. According to the analysis of this rhythm and of the series of accelerations and decelerations, the device evaluates the presence of an arrhythmia susceptible of being treated.

European patent No. 360,412 bases its interpretation of the tachycardia type on a classification, into several adjoining regions, of the rhythms analyzed from the cardiac signal detected in the ventricle.

These two systems have the drawback of relying solely on the signals picked up in one single cardiac chamber. It is difficult for devices that only detect the occurrence of tachycardia from signals picked up in the ventricle to distinguish SVT and VT conditions.

U.S. Pat. No. 4,860,749 describes a device that picks up the signals representative of the cardiac activity in both the ventricle and the atrium. The device defines different types of tachycardia by means of an algorithm using several rate thresholds and comparison with delays introduced into the device for each patient.

However, due to the numerous tests that must be conducted, such an algorithm is difficult to use in an implantable device.

SUMMARY OF THE INVENTION

It is, therefore, an object of this invention to provide a system that can be incorporated into an implantable cardiac pacemaker or defibrillator, that is capable of simultaneously sensing the cardiac activity in the atrium and in the ventricle to distinguish between SVT and VT conditions and optionally command an appropriate therapeutic mode. It is another object to establish the distinction by easily implemented software in a microprocessor controlled device.

It is a further object of this invention to provide an apparatus and a method of analysis of cardiac activity for establishing a distinction between the VT and SVT tachycardias within a short period of time.

Broadly, the present invention is directed to improved methods and apparatus for analysis of cardiac activity for an implantable tachycardia treatment device which senses the signals coming from the atrium and the signals coming from the ventricle and analyses these signals to discriminate VTs from SVTs and apply the correct therapeutic treatment. One such analysis is characterized by:

calculating a divergence of RR intervals, dRR, the interval being calculated between two successive ventricular R wave events;

calculating a divergence of PR intervals, dPR; the PR interval being measured between an R wave and the P wave immediately preceding said R wave;

triggering a signal corresponding to a ventricular tachycardia (VT) when the calculated divergence dPR exceeds the calculated divergence dRR by a first determined value; and triggering a signal corresponding to a supraventricular tachycardia (SVT) when the calculated divergence dRR exceeds the calculated divergence dPR by a second determined value. The first and second determined values may be absolute values or relative values.

Another aspect object of the invention is directed to a system of analysis of cardiac activity, for use in an implantable tachycardia treatment device, such as a cardiac pacemaker or defibrillator of the type in which the signals coming from the atrium and the signals coming from the ventricle are sensed and analyzed. One such system is characterized by a microprocessor-equipped device that is further programmed with functions:

to determine RR intervals and PR intervals;

to analyze, cycle by cycle, over a sliding window of programmable duration, the divergence dRR between RR intervals and the divergence dPR between RR intervals;

to trigger a first signal corresponding to a ventricular tachycardia condition when the determined divergence dPR exceeds the determined divergence dRR by a first determined value; and to trigger a second signal corresponding to a supraventricular tachycardia condition when the determined divergence dRR exceeds the determined divergence dPR by a second determined value.

In a preferred embodiment, the determined divergence dPR between the PR intervals is measured, cycle by cycle, as the absolute value of the difference between two successive PR intervals (i) and (i−1) as follows:

$$dPR = ABS|PR(i) - PR(i-1)|.$$

In another embodiment, the determined divergence dPR is taken as the maximum value of all of the divergences dPR measured during each cycle within a sliding window of programmable duration.

In yet another embodiment, the determined divergence dPR is measured, at each cycle, as the difference between the biggest and the smallest measured PR interval during the sliding window of programmable duration.

In a preferred embodiment, the determined divergence dRR is measured, at each cycle, as the difference between the biggest and the smallest measured RR interval during a sliding window of programmable duration.

Each of the sliding windows for the determined divergences dPR and dRR corresponds to a duration selected of from 2 to 32 ventricular cycles, more preferably 8 to 16 cycles, and even more preferably 8 cycles.

The first determined value is preferably an absolute threshold value S1. The second determined value is preferably an absolute threshold value S2. The difference of the determined divergences between PR intervals on the one part and dRR between RR intervals on the other part, is measured and compared with said threshold values S1 and S2. Each of the two threshold values (S1, S2) is selected from between 0 and 150 ms in absolute value. Preferably, the two threshold values (S1, S2) are chosen to be equal, more preferably equal to zero.

Within the sliding window, a tachycardia type, ventricular or supraventricular, is characterized when the corresponding threshold value, S1 or S2 respectively, is exceeded a selected number of times, corresponding to a predetermined percentage of the number of cycles in the sliding window. The percentage is selected from between 50% and 100%, and is preferably equal to 75%.

BRIEF DESCRIPTION OF THE DRAWING

Further features and advantages of the invention will be apparent upon consideration of the foregoing objects and the following detailed description of a preferred embodiment of the present invention, taken in conjunction with the accompanying drawing in which.

DETAILED DESCRIPTION OF THE INVENTION

Figure 1:
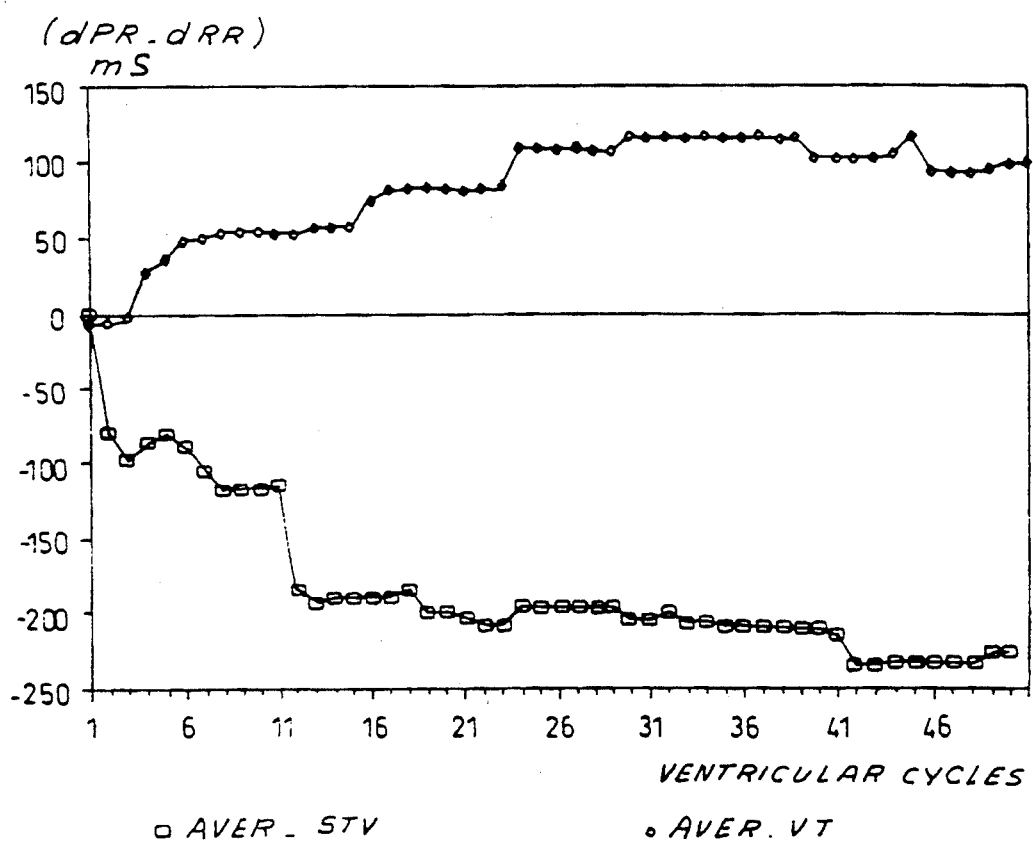
FIG. 1 is a representative plot of the results of the measurements (dPR−dRR) along the Y-axis, as a function of the number of cardiac cycles, on the X-axis, for 20 patients. The statistical difference (dPR−dRR) is negative for the 8 patients having the characteristics of a SVT and is positive for the 12 patients having the characteristics of a VT.

In the present invention, at each ventricular cycle within a sliding window selected in a range of from 2 to 32 cycles, and preferably of from 8 to 16 cycles, the PR and RR intervals are measured. The P-R interval is measured between an R wave and the P wave immediately preceding that R wave. Within the sliding window, the device, e.g., by means of a microprocessor-equipped device sensing atrial and ventricular depolarizations, measures the divergences dPR of the measured PR intervals, the divergences dRR of the measured RR intervals, and the difference of the measured divergences (dPR−dRR).

The divergences dPR are measured in absolute value of the cycle by cycle difference between the PR intervals:

$$dPR = ABS|PR(i) - PR(i-1)|$$

In one embodiment the measurement of the divergence dPR can be taken as the maximum value of the divergence dPR measured during a sliding window of programmable duration.

In an alternative embodiment, the measurement of the divergence dPR can be the difference between the longest PR interval and the shortest PR interval sensed within the sliding window of cycles. The divergence in this case is then:

$$dPR = (PR\max - PR\min)$$

The divergences dRR are preferably measured by the difference between the longest RR interval and the shortest RR interval sensed within the sliding window of cycles, i.e.:

$$dRR = (RR\max - RR\min)$$

The difference (dPR−dRR) is then compared to two threshold values, S1 and S2, each of which is selected from between 0 and 150 ms in absolute value.

The threshold value S1 is positive or zero. The threshold value is negative or zero. The threshold values S1 and S2 can have different absolute values, e.g.:
S1 = +50 ms; S2 = −30 ms
They can have the same absolute value, e.g.:
S1 = +30 ms; S2 = −30 ms
They can be equal to one another and equal to zero as in the two threshold lines merging with the X-axis illustrated in FIG. 1.

When the difference (dPR−dRR) exceeds the first threshold value S1, a ventricular tachycardia is characterized for the current cardiac cycle.

When the difference (dPR−dRR) is lower than the second threshold value S2, a supraventricular tachycardia is characterized for the current cardiac cycle.

Preferably, in the sliding window, e.g., of 8 ventricular cycles, a statistical determination of the tachycardia type can be envisaged. In this case, if out of 8 ventricular cycles, the difference (dPR−dRR) exceeds a threshold value, e.g., S1, a number of times corresponding to a given percentage, e.g. 75% (i.e., for six out of eight cycles), the corresponding tachycardia can be deemed characterized as a ventricular tachycardia. The same scenario and percent may be applied for threshold S2 and characterizing supraventricular tachycardias.

In the above described example, the threshold values S1 and S2 correspond with determined absolute values. However, in an alternative embodiment of the invention, the values S1 and S2 can be relative values, and correspond to delta % functions of the divergences, such as (dPR−dRR)/dRR, and (dRR−dPR)/dPR, respectively.

The result of the discrimination between SVT and VT is to generate respective trigger signals which can be used to apply to the appropriate selected programmed therapy. This may be achieved by the microprocessor providing a suitable command to a stimulating pulse generator for providing the cardioversions or defibrillation pulse (or pulse sequence) on one or more of the cardiac or defibrillator leads.

The system embodying the invention includes a device with two cardiac leads, one atrial and the other ventricular, and of a software program or solid state finite state machine for the automatic computation of the RR and PR intervals, divergences dPR and RR, and the difference of determined divergences (dPR−dRR). The detection of atrial and ventricular complexes (depolarizations) and the measuring of these complexes and noted intervals are performed by conventional electronic means, e.g., digital microprocessor controlled devices having atrial and ventricular sense amplifiers, signal conditioning circuits, analog-to-digital conversion circuits, and suitable memory and registers for time-based digital data processing and manipulation. Representative electronic circuits for acquiring the cardiac signals and PR and RR intervals are those found in the series of dual chamber pacemakers available from Ela Medical, Montrouge, France, offered under the CHORUS trademark. The present invention is preferably implemented in software and is specifically applied following acquisition of the cardiac electric signals by conventional sense amplifiers, more preferably after the acquired signals have been conditioned and converted to digital form in the usual manner.

One skilled in the art will appreciate that the present invention can be practiced by other than the preferred embodiments, which are presented for purposes of illustration and not of limitation.

We claim:

1. A method of analysis of cardiac activity for an implantable tachycardia sensing device which detects and analyzes the signals coming from the atrium and the ventricle, characterized by:
   detecting R waves from the ventricle and P waves from the atrium;
   determining an RR interval between successive sensed R waves corresponding to a cardiac cycle;
   determining a PR interval between an R wave and the P wave immediately preceding said R wave, for said cardiac cycle;
   calculating a divergence of RR intervals dRR;
   calculating a divergence of PR intervals dPR;
   determining a difference between the calculated divergences dPR and dRR and comparing said difference to at least one of a first value and second value;
   triggering a first signal corresponding to a ventricular tachycardia when the calculated divergence dPR exceeds the calculated divergence dRR by said first value; and
   triggering a second signal corresponding to a supraventricular tachycardia when the calculated divergence dRR exceeds the calculated divergence dPR by said second value.

2. The method of claim 1 wherein the step of calculating the divergence dPR further comprises measuring two successive PR intervals and taking the absolute value of the difference between said two successive PR intervals according to the formula:

$$dPR = ABS|PR(i) - PR(i-1)|$$

where (i) is one cardiac cycle and (i−1) is preceding cardiac cycle.

3. The method of claim 2 further comprising providing a sliding window of a duration wherein the step of calculating the divergence dPR further comprises calculating the divergence PR for each cardiac cycle in said sliding window, analyzing said calculated divergences dPR during said sliding window and selecting the maximum value of said analyzed divergences.

4. The method of claim 3 wherein providing said sliding window further comprises providing a programmable sliding window duration that is programmed to a duration selected in the range of from 2 to 32 cardiac cycles.

5. The method of claim 4 further comprising programming the sliding window duration to 8 ventricular cardiac cycles.

6. The method of claim 1 further comprising providing a sliding window of a duration wherein the step of calculating the divergence dPR further comprises determining the PR intervals for each cardiac cycle in said window, analyzing said determined PR intervals during said sliding window, determining the biggest and the smallest of said measured PR intervals during said window, and calculating the divergence dPR as the difference between said determined biggest and smallest measured PR intervals, wherein said divergence dPR is recalculated each cardiac cycle.

7. The method of claim 6 wherein providing said sliding window further comprises providing a programmable sliding window duration that is programmed to a duration selected in the range of from 2 to 32 cardiac cycles.

8. The method of claim 7 further comprising programming the sliding window duration to 8 ventricular cardiac cycles.

9. The method of claim 1 further comprising providing a sliding window of a duration, wherein the step of calculating the divergence dRR further comprises determining the RR intervals for each cardiac cycle in said sliding window, analyzing said determined RR intervals, determining the biggest and the smallest of said determined measured RR intervals during said sliding window and determining the divergence dRR as the difference between said determined biggest and smallest RR intervals, wherein said divergence RR is redetermined each cardiac cycle.

10. The method of claim 9 wherein providing said sliding window further comprises providing a programmable sliding window duration that is programmable to a duration selected in the range of from 2 to 32 cardiac cycles.

11. The method of claim 10 further comprising programming the sliding window duration to 8 ventricular cardiac cycles.

12. The method as claimed in claim 1, further comprising providing the first value as an absolute threshold value S1, providing the second value as an absolute threshold value S2, and wherein determining the difference of the calculated divergences dPR and dRR further comprises comparing said difference to said threshold values S1 and S2.

13. The method of claim 1 further comprising providing each of the first and second values as a value selected from between 0 and 150 ms.

14. The method as claimed in claim 13 further comprising providing the first and second values as equal in value.

15. The method of claim 14, further comprising providing the first and second values as equal to zero.

16. The method of claim 1 further comprising providing a sliding window of a programmable duration, the programmable duration being selected from between 2 and 32 cardiac cycles and determining said difference between said calculated divergences and comparing said difference to at least one of said first and second values for each cycle in said sliding window.

17. The method of claim 16 further comprising programming the programmed duration to be from between 8 and 16 cardiac cycles.

18. The method of claim 16 wherein triggering the first signal further comprises determining the number of times the first value is exceeded during said sliding window, and triggering said first signal when said number is greater than a percentage of the number of cardiac cycles in the window, and wherein triggering the second signal further comprises determining the number of times the second value is exceeded during said sliding window, and triggering said second signal when said number is greater than said percentage of the number of cardiac cycles in the window.

19. The method of claim 18 further comprising selecting the percentage to be on the order of 75%.

20. The method of claim 1 further comprising providing the first and second values as relative values based on the determined divergences dPR and dRR.

21. A system of analysis of cardiac activity, for an implantable tachycardia treatment device, such as a microprocessor-equipped pacemaker, cardioverter or defibrillator having an atrial lead and a ventricular lead for sensing the signals coming from the atrium and the ventricle, comprising:
  means for determining RR intervals and PR intervals, an RR interval being measured between successive R waves corresponding to a cardiac cycle, a PR interval being measured between an R wave and the P wave immediately preceding said R wave;
  means for providing a sliding window of programmable duration corresponding to a plurality of cardiac cycles;
  means for determining the divergences dRR between RR intervals and the divergences dPR between PR intervals during said sliding window;
  means for determining a difference between said calculated divergences dPR and dRR and comparing said differences to at least one of a first value and a second value, said divergences and said difference being determined with each new cardiac cycle;
  first means for triggering a first signal corresponding to a ventricular tachycardia condition when the determined divergence dPR exceeds the determined divergence dRR by said first value;
  second means for triggering a second signal corresponding to a supraventricular tachycardia condition when the determined divergence dRR exceeds the determined divergence dPR by said second value; and
  means for delivering a treatment for ventricular tachycardia in response to said first signal and for not delivering said ventricular tachycardia treatment in response to said second signal.

22. The system of claim 21 further comprising means for providing the first and second values as one of absolute values selected from between 0 and 150 ms and relative values based on the determined divergences dPR and dRR.

23. Apparatus for analysis of cardiac activity, for an implantable tachycardia sensing device, which detects and analyzes the signals coming from the atrium and from the ventricle comprising:
  means for determining RR intervals and PR intervals, the RR intervals being measured between successive R waves corresponding to a cardiac cycle, the PR intervals being measured between an R wave and the P wave immediately preceding said R wave;
  first means for calculating a divergence dRR of RR intervals;
  second means for calculating a divergence dPR of PR intervals;
  means for determining a difference between the calculated divergences dPR and dRR;
  means for comparing the determined difference to at least one of a first value and a second value;
  means for triggering a first signal corresponding to a ventricular tachycardia condition when the calculated divergence dPR exceeds the calculated divergence dRR by said first value; and
  means for triggering a second signal corresponding to a supraventricular tachycardia condition when the calculated divergence dRR exceeds the calculated divergence dPR by said second value.

24. The apparatus of claim 23 wherein the second calculating means calculates the divergence dPR as the absolute value of the difference between two successive PR intervals, such that a divergence dPR is calculated each cardiac cycle.

25. The apparatus of claim 24 wherein the second calculating means further comprises means for defining a sliding window of a duration and means for selecting the calculated divergence dPR as the maximum value of the divergences dPR calculated during said sliding window.

26. The apparatus of claim 25 wherein said defining means sliding window duration corresponds to a duration selected in the range of from 2 to 32 cardiac cycles.

27. The apparatus of claim 26 wherein said defining means sliding window duration corresponds to 8 ventricular cycles.

28. The apparatus of claim 23 wherein the second calculating means further comprises means for defining a sliding window of a duration and means for determining the calculated divergence dPR as the difference between the biggest and the smallest determined PR intervals during said sliding window, said calculated divergence being redetermined each cardiac cycle.

29. The apparatus of claim 28 wherein said defining means sliding window duration corresponds to a duration selected in the range of from 2 to 32 cardiac cycles.

30. The apparatus of claim 29 wherein said defining means sliding window duration corresponds to 8 ventricular cycles.

31. The apparatus of claim 23 wherein the first calculating means further comprises means for defining a sliding window of a duration and means for determining the calculated divergence dRR as the difference between the biggest and the smallest determined RR intervals during said sliding window said calculated divergence being redetermined each cardiac cycle.

32. The apparatus of claim 31 wherein said defining means sliding window duration corresponds to a duration selected in the range of from 2 to 32 cardiac cycles.

33. The apparatus of claim 32 wherein said defining means sliding window duration corresponds to 8 ventricular cycles.

34. The apparatus as claimed in claim 23, wherein said comparing means is characterized by the first value being an absolute threshold value S1, and the second value being an absolute threshold value S2.

35. The apparatus of claim 23 wherein the first and second values are selected from between 0 and 150 ms in absolute value.

36. The apparatus of claim 35 wherein the first and second values are equal in absolute value.

37. The apparatus of claim 36, wherein the first and second values are equal to zero.

38. The apparatus of claim 23 further comprising means for defining a sliding window of programmable duration, the programmable duration being selected from between 2 and 32 cardiac cycles wherein said difference determining means determines the differences of said calculated divergences dPR and dRR during said sliding window.

39. The apparatus of claim 38 wherein said programmed duration is selected from between 8 and 16 ventricular cycles.

40. The apparatus of claim 38 further comprising means for determining the number of times the first value is exceeded during said sliding window, means for determining the number of times the second value is exceeded during said sliding window, wherein the first signal triggering means triggers the first signal in response to the first value being exceeded a number of times corresponding to a percentage of the number of cardiac cycles in the sliding window, and wherein the second signal triggering means triggers the second signal in response to the second value being exceeded a number of times corresponding to a said percentage of the number of cardiac cycles in the sliding window.

41. The apparatus of claim 40 wherein said percentage is on the order of 75%.

42. The apparatus of claim 23 further comprising means for providing the first and second values as relative values based on the determined divergences dPR and dRR.

* * * * *

UNITED STATES PATENT AND TRADEMARK OFFICE
CERTIFICATE OF CORRECTION

PATENT NO. : 5,325,856
DATED : July 5, 1994
INVENTOR(S) : Nitzsche et al.

It is certified that error appears in the above-indentified patent and that said Letters Patent is hereby corrected as shown below:

Column 1, line 63, delete "is", second occurrence;

Column 2, line 32, after "aspect" delete "object";

Column 2, line 45, "between RR" should be --between PR--;

Column 3, line 52, "P-R" should be --PR--;

Column 4, line 22, after "value" insert --S2--;

Signed and Sealed this

Fourth Day of April, 1995

Attest:

BRUCE LEHMAN

Attesting Officer

Commissioner of Patents and Trademarks